(12) United States Patent
Zwelling-Aamot

(10) Patent No.: US 6,206,839 B1
(45) Date of Patent: Mar. 27, 2001

(54) CERVICAL CANCER SELF-SCREENING METHODS AND APPARATUS

(76) Inventor: Marcy L. Zwelling-Aamot, 2425 E. Ocean Blvd., Long Beach, CA (US) 90803

( * ) Notice: Subject to any disclaimer, the term of this patent is extended or adjusted under 35 U.S.C. 154(b) by 0 days.

(21) Appl. No.: 09/232,514

(22) Filed: Jan. 15, 1999

(51) Int. Cl.⁷ .................................................. A61B 10/00
(52) U.S. Cl. ............................................................ 600/572
(58) Field of Search .................................. 600/562, 569, 600/570, 572

(56) References Cited

U.S. PATENT DOCUMENTS 3,842,166 * 10/1974 Bucalo .................................. 600/562
3,881,464 * 5/1975 Levene .................................. 600/569
5,348,023 * 9/1994 McLucas .............................. 600/570
5,370,128 * 12/1994 Wainwright ......................... 600/569

* cited by examiner

Primary Examiner—Cary O'Connor
Assistant Examiner—Pamela L. Wingood
(74) Attorney, Agent, or Firm—Oppenheimer Wolff & Donnelly LLP

(57) ABSTRACT

An insert for the passive, painless, noninvasive self-collection of free endocervical cells by a subject includes a body and a substrate for cell collection. The body has a proximal end for manipulation by the subject and a distal end on which the cell-collecting substrate is disposed. The body is configured so that the substrate is positionable by the subject within the vagina, preferably near the vaginal portion of the cervix, to allow collection of free endocervical cells onto the cell-collection surface. After cells have been collected, the subject may place the cell-retaining substrate into a cell-suspension preservative contained in a sealable receptacle for transport to a laboratory for conventional analysis.

24 Claims, 1 Drawing Sheet

CERVICAL CANCER SELF-SCREENING METHODS AND APPARATUS

FIELD OF THE INVENTION

Broadly stated, the present invention relates to cancer screening methods and apparatus. More particularly, the present invention is directed to a simple and accurate method and associated apparatus that will allow a female patient to collect cervical cells in the privacy of her home as part of a cervical cancer-screening test. The apparatus of the present invention is easy and inexpensive to manufacture and, used in accordance with the method of the invention, will enhance patient compliance with recommended cervical cancer-screening protocols.

BACKGROUND OF THE INVENTION

In the early 1900s, cervical cancer was the leading cause of cancer death for women. Even today, after nearly 100 years of continued medical research and development, cervical cancer continues to be the leading cause of cancer death for women in developing countries. These deaths are completely unnecessary because up to 90% of the most common types of cervical cancer may be prevented if identified early and treated. The present invention facilitates this early identification and subsequent treatment.

In spite of the ability of modem medical practitioners to effectively eradicate most types of cervical cancer, it is estimated that 100,000 new cases of cervical cancer in the United States go undetected every five years. The same characteristics of cervical cancer that make it relatively easy to treat once identified contribute to the difficulty in its detection. In its early stages of development, cervical cancer grows contiguously in localized, defined sites and does not interfere with other normal bodily functions. Thus, at these early stages, cervical cancer can be relatively asymptomatic and can continue to grow and progress for years with little indication other than minor, localized bleeding which can be dismissed as normal "spotting." Left unchecked for a year or more, cervical cancer can spread beyond the cervix without warning. At this point, once detected, the cancer may be so advanced that it may likely be untreatable and may ultimately lead to the patient's death.

Conversely, if detected early there are two effective forms of treatment for removing abnormal tissue from the cervix. In one procedure, the abnormal tissue is removed from the cervix in a cryosurgical procedure wherein the surface of the cervix is frozen. Alternatively, abnormal cervical tissue can be cauterized with a heated surgical apparatus. Both treatments are commonly performed in a doctor's office on an out-patient basis following a confirming biopsy. Post-surgical impact on the patient is relatively minor and short lasting.

The key to successful eradication of cervical cancer is early detection. For the last 50 years, a safe and effective cervical cancer-screening test has been available which can detect very early changes in cervical tissues long before any other symptoms develop. Known as the Pap Screening Test, or "Pap Smear," this test is a microscopic examination of a prepared glass slide containing a smear or sample of cells collected from the opening and outer portion of a patient's cervix by a healthcare professional during a pelvic exam.

The Pap-screening test is relatively simple and takes only a few minutes to perform. A physician or other healthcare professional inserts a special instrument known as a speculum into the patient's vagina to hold the vaginal walls apart so that the surface of the cervix can be directly observed and accessed. The lining or surface of the cervix is made up of millions of tiny cells. A sample of these cells is collected or "harvested" by the physician or healthcare professional utilizing a tiny spatula-like instrument or swab to scrape or rub cells from the cervical oz, from the surrounding cervical fornix, or from any suspicious-looking or abnormal areas on the cervix. These harvested cells are transferred directly to a glass slide where they are "smeared" into a thin layer, which is then stained and viewed under a microscope. Typically, the smeared glass slide is sent to a professional clinical laboratory for the microscopic examination. However, the slide can also be examined in the physician's office. Sometimes abnormal or pre-cancerous cells develop in the cervical lining, and, after staining, these cells can be readily identified under the microscope. If identified, these pre-cancerous changes, called "displasia," justify further testing, which may include a surgical "biopsy" wherein a small piece of tissue from the suspicious area is collected and examined. Because these pre-cancerous changes can grow and spread and may lead to cancer if left untreated, a positive biopsy result may justify removal of the abnormal cervical tissue.

More recently, an improved Pap-screening test has been developed utilizing the same cervical cell-collecting procedures as previously described, but adding the additional step of suspending the collected cells in a solution prior to making the smear on the glass slide. The cell suspension is sent to the laboratory to be read, whereupon the laboratory pathologist spins or centrifuges the suspension to deposit the cells in a thin, single cell layer on the slide. This procedure eliminates cell clumping and provides the pathologist with a smear that is easier to read correctly, thereby reducing the number of false positive test results.

In spite of the Pap-screening test's 50-year record of safety and accuracy, at least 35% of women in the United States between the ages of 15 and 44 do not schedule a regular visit for this vital screening exam. Thus, patient noncompliance is the biggest issue that must be overcome in order to reduce the incidence of cervical cancer. Presently, medical professionals recommend an annual Pap-screening test for every sexually active women up to age 70. Monogamous women with up to three normal Pap-screening tests in a row can decrease the recommended screening interval to once every three years. In spite of these recommendations, cervical cancer continues to exhibit two age-related peaks in the susceptible population for women in their 20s and again in their 50s. If identified early during the in situ stage before the cancer has invaded other tissues, then this completely unnecessary disease can be eliminated by resecting the cancerous tissue from the cervix. Nonetheless, patient compliance remains the biggest obstacle to this objective because even though the Pap-screening test is relatively noninvasive and quick, it remains physically and psychologically uncomfortable for most female patients. Compounding matters, in today's modem world, it is becoming increasingly more difficult for women to fit medical appointments into their busy daily schedules. Further compounding matters, socioeconomic pressures may make it difficult if not impossible for many women to afford the cost of a medical visit and subsequent laboratory analysis. In developing countries, the simple absence of trained healthcare professionals and laboratory facilities may make these screening tests impossible to administer to the population at large.

Accordingly, it is a primary objective of the present invention to provide effective methods and apparatus that will facilitate the collection or harvesting of endocervical cells making up the lining of the cervical mucosa or mucus membranes in a manner that will readily interface with existing cervical cancer-screening laboratory techniques.

It is an additional object of the present invention to provide effective methods and apparatus for cervical cancer-screening tests which can be self-administered without the need for direct cervical observation or access or without the assistance of healthcare professionals.

It is a still further object of the present invention to provide cervical cancer self-screening methods and apparatus which are inexpensive to produce and distribute and which can be made widely available to the consuming public.

BRIEF SUMMARY OF THE INVENTION

These and other objects are achieved by the methods and apparatus of the present invention which enable women to perform self-screening tests on their own without the assistance of healthcare practitioners and without invasive, direct-observation cell collection procedures.

According to one aspect of the invention, apparatus for the self-collection of free endocervical cells by a subject includes an insert and a sealable receptacle. The insert includes a body and a substrate for cell collection. The body has a proximal end for manipulation by the subject and a distal end on which the substrate is disposed. The substrate has a cell-collection surface. The body is configured so that the substrate is positionable by the subject within the vagina, preferably near the vaginal portion of the cervix, to allow collection of free endocervical cells onto the cell-collection surface. After cells have been collected, the subject places the cell-retaining substrate into a preservative in the sealable receptacle for transport to a laboratory for traditional analysis.

The body may include a carrier disposed on the distal end for retaining the substrate. The carrier may be configured to complement the anatomical shape of the vaginal portion of the cervix uteri; for example, the carrier may be substantially cup shaped. In this embodiment of the insert, the substrate is disposed on a distal portion of an outer surface of the carrier. Alternatively, the carrier may be substantially bulb shaped. When the insert is positioned in the vagina, contact with the vaginal portion of the cervix is not necessary for the collection of cells. In this regard, a gap may be present between the cell-collecting surface of the insert and the vaginal portion of the cervix without negatively affecting the ability of the insert to collect cervical cells.

In accordance with the present invention, a subject may perform a passive, pain-free cervical cell-collection procedure in private without the assistance of a healthcare practitioner, without undergoing invasive procedures, and without being subject to invasive instruments such as a speculum. Accordingly, the screening method of the present invention may be performed by the subject alone at the subject's home. The self-screening by a subject in accordance with the present invention runs counter to conventional wisdom that screening must be executed by a doctor viewing the cervix directly and then "harvesting" cells specifically targeted by the doctor through direct, physical contact with the cervix. The cost of performing a screening test is, therefore, greatly reduced. In addition, women are more likely to perform regular screenings on themselves because of the noninvasive, simple, private, and economical procedure of the invention, thereby greatly enhancing screening compliance. Furthermore, self-screening kits produced in accordance with the teachings of the present invention, including an insert and a preservation receptacle, may be packaged for retail sale or for mass distribution, particularly to underdeveloped countries where shortages of doctors prevent most women from undergoing screening tests.

Further objects, features, and advantages of the cervical cancer self-screening methods and apparatus of the present invention, as well as a better understanding thereof, will be afforded to those skilled in the art from a consideration of the following detailed explanation of exemplary embodiments thereof, taken in conjunction with the accompanying drawings which illustrate, by way of example, the principles of the present invention.

DETAILED DESCRIPTION OF THE INVENTION

Figure 1:
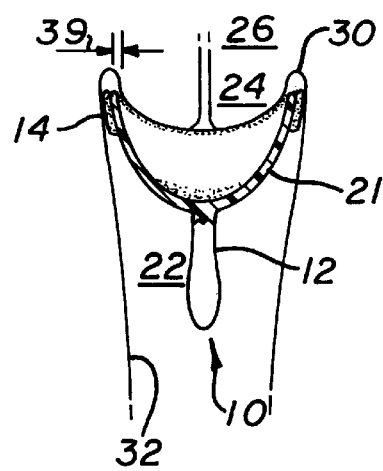
FIG. 1 is a cross-sectional view of a cell-collection device in accordance with an exemplary embodiment the present invention, particularly illustrating the device positioned within a vaginal canal.
Figure 2:
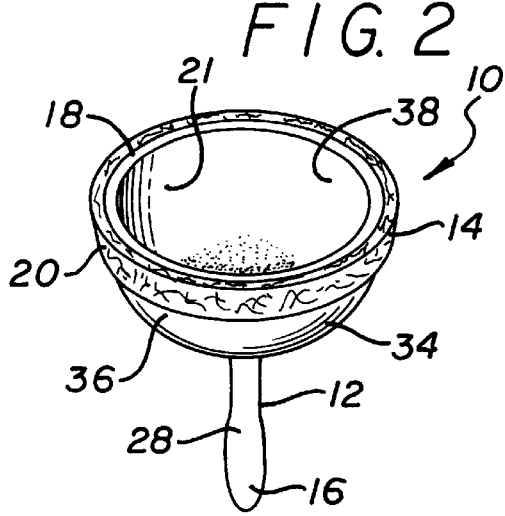
FIG. 2 is a perspective view of the cell-collection device of FIG. 1.

Referring more particularly to the drawings, an exemplary cervical cell-collection insert 10 configured and utilized in accordance with the teachings of the present invention is illustrated in FIGS. 1 and 2. Exemplary insert 10 generally includes a body 12 and a cell-collection substrate 14. The body 12 has with a proximal end 16 and a distal end 18, with the substrate 14 disposed on the distal end 18 of the body. Exemplary substrate 14 has a cell-collection surface 20 adapted to retain free endocervical cells. The substrate 14 is mad from material that either absorbs or adsorbs free endocervical cells, for example, cotton or porous elastomeric or fibrous materials. Alternatively, rather than being provided with a dedicated additional structure, exemplary insert 10 may not include a substrate but may rather have the surface of the distal end 18 of the body 12 define a cell-collection surface, indicated by numeral 21, which will be discussed in more detail below.

As particularly shown in FIG. 1, the body 12 of exemplary insert 10 is configured so that a subject may position the substrate 14 within the vagina 22 to allow collection of free endocervical cells onto the cell-collection surface 20. More specifically, the body 12 is preferably configured so that the subject may position the substrate 14 within the vagina 22 to be near the vaginal portion 24 of the cervix uteri 26. In embodiments of the insert 10 without a dedicated substrate, the collection of cervical cells takes place on the cell-collection surface 21 of the distal end 18 of the body 12. Even with the provision of the substrate 14, cervical cells may be collected by the cell-collection surface 21 of the body 12 itself. The body 12 may include a handle 28 disposed on the proximal end 16 to facilitate the positioning of the cell-collection surface 20 (and 21) within the vagina 22. Those skilled in the art will appreciate that the handle 28 is not essential to the practice of the present invention. Supplementing anatomical reference numerals 22, 24, and 26 that respectively indicate the vagina, the vaginal portion of the cervix, and the cervix itself, reference numeral 30 indicates the fornices of the vagina in general, and reference numeral 32 indicates the vaginal orifice.

In addition to the handle 28 disposed on the proximal end 16, the body 12 may include a carrier 34 disposed on the distal end 18 for retaining the substrate 14. In the exemplary embodiment of the cell-collection insert 10 shown in FIGS. 1 and 2, the carrier 34 is configured to complement the anatomical shape of the vaginal portion 24 of the cervix 26. More specifically, the carrier 34 is hemispherical or cup shaped with an outer surface 36 and an inner surface 38. In the cup-shaped embodiment, the substrate 14, if present, may be disposed on at least a distal portion of the outer surface 36 of the carrier 34. In this embodiment, the substrate 14 is provided to illustrate additional alternative features of the present invention and may be described as an annular ring disposed on a plunger-like body 12. Alternatively, the substrate 14 may also be disposed on at least a distal portion of the inner surface 38 of the carrier 4 (not shown), or may extend from the outer surface 36 to the inner surface 38, encasing the distal end 18 of the body 12 (not shown).

As shown in FIG. 1, the cup-shaped carrier 34 is positionable near or about the vaginal portion 24 of the cervix 26, with the distal portion thereof with the substrate 14 positionable at or near the fornices 30 of the vagina 22. It should be emphasized that contact with the vaginal portion 24 of the cervix 26 or sealing with the vaginal walls is not necessary to practice the present invention, though it may occur without affecting the performance of the present invention. In this regard, a gap 39 may be present between the insert 10 and the vaginal portion 24 of the cervix 26 when the insert is positioned within the vagina 22 for the collection of cells.

Figure 3:
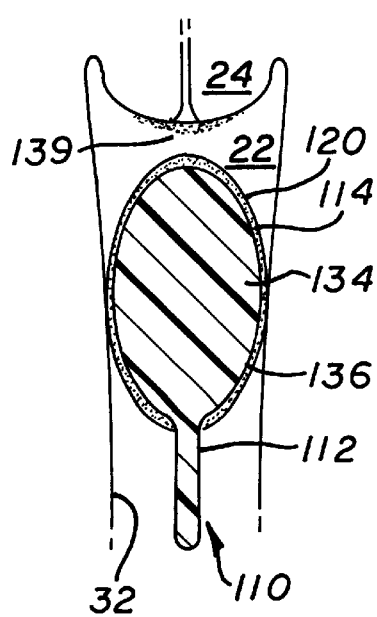
FIG. 3 is a cross-sectional view of a cell-collection device in accordance with an alternative exemplary embodiment of the present invention, particularly illustrating the device positioned within a vaginal canal.

Rather than being substantially cup shaped, the carrier may be bulb shaped, as shown in FIG. 3. For the purposes of this description, elements of the cell-collection insert of the invention that are analogous in function to elements previously described are indicated with like reference numerals with the addition of a "1" prefix; for example, the substrate of the invention is indicated by numeral 14 in FIG. 2 and by numeral 114 in FIG. 3 (and by numeral 214 in FIG. 4). In the exemplary embodiment of the cell-collection insert 110 shown in FIG. 3, the substrate 114 is disposed substantially about the outer surface 136 of the bulb-shaped carrier 134 of the body 112. More specifically, exemplary substrate 114 illustrated in FIG. 3 is a layer of material encasing the carrier 134. As shown, the substrate 114 is insertable through the vaginal orifice 32 and positionable within the vagina 22, somewhere near the vaginal portion 24 of the cervix, thereby enabling the cell-collection surface 120 of the substrate to retain free endocervical cells. Contact with the vaginal portion 24 of the cervix 26 is not necessary for the collection of cells by the insert 10 of the invention, as shown by the gap 139.

Figure 4:
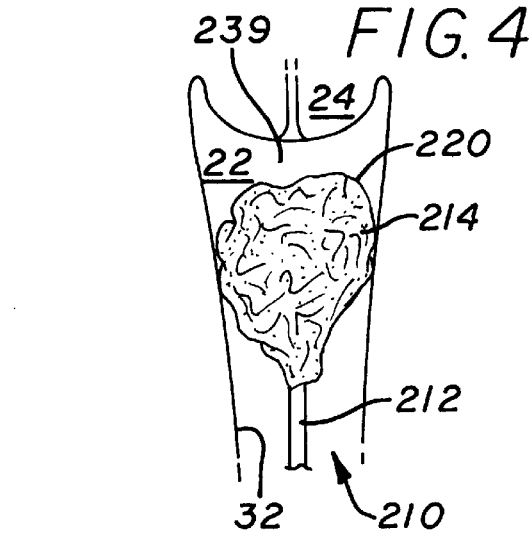
FIG. 4 is a cross-sectional view of a cell-collection device in accordance with yet another alternative embodiment of the present invention, particularly illustrating the device positioned within a vaginal canal.

Referencing FIG. 4, rather than being configured with a dedicated carrier, the body 212 of exemplary insert 210 retains the substrate 214 on the distal end thereof. In this embodiment, exemplary substrate 214 is a swab of material attached to the distal portion of the body 212. Once again, the substrate 214 is insertable through the vaginal orifice 32 and positionable within the vagina 22, at or near the vaginal portion 24 of the cervix, thereby enabling the cell-collection surface 220 of the substrate to retain free endocervical cells. Although contact may occur without negatively affecting the collection of cells, a gap 239 may be present between the swab-like substrate 214 and the vaginal portion 24 of the cervix 26.

To use exemplary inserts 10 (110, 210) in a self-screening procedure, a subject holds the proximal portion 16 of the body 12 to insert the substrate 14 through the vaginal orifice 30 to be positioned within the vagina 22 and, more preferably, at or near the vaginal portion 24 of the cervix 26. After a predetermined period of time, the subject removes the substrate 14. The predetermined period of time may range from, for example, as little as a few minutes to tens of minutes. Alternatively, the insert 10 (or at least the cell-collection substrate 14) may be left in place for extended periods of time, for example, overnight. The predetermined period of time is sufficient to allow collection of a sufficient number of cells to enable an analysis to take place. As cells continually slough from the cervix 26, tens or hundreds of cells (sufficient for analysis may be collected on the cell-retaining outer surface 20 of the substrte 14 in a matter of minutes.

Figure 5:
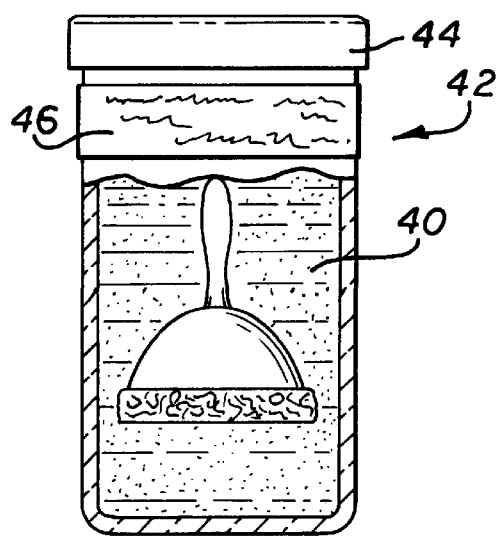
FIG. 5 is a partial cross-sectional view of a sample container of the present invention, particularly illustrating a cell-collection device immersed in a transport medium within the sample container.

After removal, the subject suspends and preserves the collected cells on the now cell-retaining substrate 14 for transport to a laboratory and for subsequent analysis. To do so, with reference to FIG. 5, the substrate 14 may be immersed in a preservative 40. More specifically, after the cell-collecting procedure described above, the insert 10 may be placed in a receptacle 42 holding the preservative 40. The receptacle 42 is preferably releasably sealable with a lid 44 and may include a label 46 on which information pertaining to the subject may be written. Although FIG. 5 illustrates the entire insert 10 held within the transport receptacle 42, only the cell-retaining substrate 14 needs to be preserved during transport to a laboratory. Accordingly, the substrate 14 may be releasably attached to the body 12 and then removed from the body 12 to be placed in the preservative 40. Alternatively, the carrier 34 may be detachable, or the insert 10 itself may be placed in the receptacle, as appropriate. After placing the substrate 14 in the preservative 40, the subject may then seal the receptacle, write identifying information on the label 46, and deliver (for example, by mail) the receptacle to a laboratory for analysis.

The preservative 40 may be any solution capable of preserving endocervical cells retained by the substrate 14 in a condition which enables proper analysis after transport to a laboratory. For example, the preservative 40 may be an aqueous solution or alcohol. An example of a commercially available preservative is PreservCyt® solution for Thin-Prep® Paptest from CYTYC Corporation of Foxborough, Mass.

As mentioned above, the substrate 14 (114, 214) is made from material that is able to retain endocervical cells either through absorption (i.e., the process of taking up or in like a sponge) or adsorption (i.e., the adhesion in an extremely thin layer of cells to the surface of a solid body). Such material may be a natural fiber such as cotton or an artificial fiber. As the endocervical cells may be suspended in the cervical mucosa, the material comprising the substrate 14 may be chosen so that such mucosa is absorbed thereby.

The substrate 14 may be either fixed or releasably attached to the distal end 18 of the body 12, for example, with adhesive of appropriate tack and biocompatibility. In an adhesive embodiment, the adhesive force retaining the substrate 14 to the body 12 needs to be greater than any force inflicted on the substrate 14 during insertion and removal to prevent inadvertent dislodging.

The body 12 is made from a biocompatible material which may be substantially rigid or, alternatively, substantially resilient. The body 12, particularly the distal end 18 (and the carrier 34) are atraumatically designed to minimize trauma to the vagina 22 and the vaginal portion 24 of the cervix 26. The carrier 34 of the body 12 may be made from a substantially flexible and resilient biocompatible material, e.g., polypropylene, so that a subject may compress the carrier 34 to facilitate insertion in the vagina 22. Such flexible and resilient material of the carrier 34 also compresses in response to removal of the insert 10 from the vagina 22.

In view of the methodology of the present invention, a subject may perform a cell-collection procedure without the assistance of a healthcare practitioner, without undergoing invasive procedures, and without being subject to invasive instruments such as a speculum. Accordingly, the screening method of the present invention may be performed by the subject alone at the subject's home. The self-screening by a subject in accordance with the present invention runs counter to conventional wisdom that screening must be done by a doctor by viewing the cervix directly (requiring a speculum) and then directly "harvesting" cells specifically targeted by the doctor through a scraping collection procedure. The cost of performing a screening test is, therefore, greatly reduced. In addition, women are more likely to perform regular screenings on themselves because of the economical and noninvasive procedure of the invention, thereby greatly enhancing screening compliance. Furthermore, self-screening kits, including an insert and a preservation receptacle, may be packaged for retail sale or for distribution, particularly to underdeveloped countries where shortages of doctors prevent most women from undergoing screening tests.

In closing, it is to be understood that the embodiments of the invention disclosed herein are illustrative of the principles of the invention and that other modifications and variations may be employed which are within the scope of the invention. Accordingly, the present invention is not limited to that precisely as shown and described in the present specification but is defined and limited only by the following claims.

What is claimed is:

1. A method for self-collecting free endocervical cells by a subject, said method comprising the steps of:
    positioning an outer cell-collection surface into the vagina to collect free endocervical cells on said cell-collection surface, said cell-collection surface adapted to collect free endocervical cells without contacting the vaginal portion of the cervix;
    removing said cell-collection surface; and
    transferring said free endocervical cells on said cell-collection surface to a preservative.

2. A method as claimed in claim 1 wherein said positioning step comprises the step of:
    positioning said cell-collection surface in the vagina for a predetermined cell-collection interval.

3. A method as claimed in claim 1 wherein said positioning step comprises the step of:
    positioning a substrate having a cell-collection surface in the vagina to collect free endocervical cells on said cell-collection surface.

4. A method as claimed in claim 1 wherein said positioning step comprises the step of:
    positioning a substrate having a cell-collection surface and disposed on a carrier in the vagina to collect free endocervical cells on said cell-collection surface.

5. A method for self-collecting free endocervical cells by a subject, said method comprising the steps of:
    positioning an outer cell-collection surface in the vagina to collect free endocervical cells on said cell-collection surface without having said cell-collection surface contact the vaginal portion of the cervix;
    removing said cell-collection surface; and
    transferring said free endocervical cells on said cell-collection surface to a preservative.

6. A method as claimed in claim 1 wherein said transferring step comprises the step of:
    transferring said endocervical cells on said cell-collection surface to a preservative retained in a sealable receptacle.

7. A method as claimed in claim 6 further comprising the additional step of:
    delivering said sealed receptacle to a laboratory.

8. Apparatus for the self-collection of free endocervical cells by a subject, said apparatus comprising:
    an insert including:
        a body having a proximal end for manipulation by the subject and a distal end with an outer cell-collection surface adapted to collect free endocervical cell without contacting the vaginal portion of the cervix;
        said body being configured so that said cell-collection surface is positionable by the subject within the vagina to allow collection of free endocervical cells onto said cell-collection surface; and
    a sealable receptacle containing a preservative for receiving free endocervical cells from said cell-collection surface.

9. Apparatus as claimed in claim 8 wherein said body is configured so that said cell-collection surface is positionable within the vagina near the vaginal portion of the cervix uteri.

10. Apparatus as claimed in claim 8 wherein said body is configured so that said cell-collection surface is positionable within the vagina without said cell-collection surface contacting the vaginal portion of the cervix uteri.

11. Apparatus as claimed in claim 8 wherein said insert further includes a substrate disposed on said body and including a cell-collection surface;
    said body being configured so that said substrate is positionable by the subject within the vagina to allow collection of free endocervical cells onto said cell-collection surface of said substrate.

12. Apparatus for the self-collection of free endocervical cells by a subject, said apparatus comprising:
    an insert including:
        a body having a proximal end for manipulation by the subject and a distal end with an outer cell-collection surface; and
        a substrate disposed on said body and including a cell-collection surface;
        said body being configured so that said cell-collection surface is positionable by the subject within the vagina to allow collection of free endocervical cells onto said cell-collection surface; and
        said body being configured so that said substrate is positionable by the subject within the vagina to allow collection of free endocervical cells onto said cell-collection surface of said substrate; and a sealable receptacle containing a preservative for receiving free endocervical cells from said cell-collection surface;

wherein said body includes a carrier disposed on said distal end for retaining said substrate.

13. Apparatus as claimed in claim 12 wherein said carrier is configured to complement the anatomical shape of the vaginal portion of the cervix uteri.

14. Apparatus as claimed in claim 13 wherein said carrier is cup shaped.

15. Apparatus as claimed in claim 14 wherein said carrier has an outer surface; said substrate being disposed on a distal portion of said outer surface of said carrier.

16. Apparatus as claimed in claim 12 wherein said carrier is bulb shaped.

17. Apparatus as claimed in claim 16 wherein said carrier has an outer surface; said substrate being disposed on at least a distal portion of said outer surface of said carrier.

18. Apparatus as claimed in claim 11 wherein said substrate is releasably attached to said body.

19. Apparatus as claimed in claim 8 wherein said body includes a handle disposed on said proximal end.

20. Apparatus as claimed in claim 8 wherein said sealable receptacle is configured to receive said cell-collection surface immersed within said preservative.

21. A method as claimed in claim 1 wherein said positioning step comprises the step of:

positioning said cell-collection surface in the vagina to collect free endocervical cells on said cell-collection surface through absorption.

22. A method as claimed in claim 1 wherein said positioning step comprises the step of:

positioning said cell-collection surface in the vagina to collect free endocervical cells on said cell-collection surface through adsorption.

23. A method as claimed in claim 11 wherein said substrate is configured to retain free endocervical cells through adsorption.

24. A method as claimed in claim 11 wherein said substrate is configured to retain free endocervical cells through adsorption.

* * * * *